US009244003B1

(12) United States Patent
Matsuo et al.

(10) Patent No.: US 9,244,003 B1
(45) Date of Patent: Jan. 26, 2016

(54) ALIGNMENT FLANGE MOUNTED OPTICAL WINDOW FOR A LASER GAS ANALYZER

(71) Applicant: YOKOGAWA ELECTRIC CORPORATION, Tokyo (JP)

(72) Inventors: Junichi Matsuo, Tokyo (JP); Alan I. Cowie, Friendswood, TX (US)

(73) Assignee: YOKOGAWA ELECTRIC CORPORATION, Tokyo (JP)

(*) Notice: Subject to any disclaimer, the term of this patent is extended or adjusted under 35 U.S.C. 154(b) by 0 days.

(21) Appl. No.: 14/620,807

(22) Filed: Feb. 12, 2015

(51) Int. Cl.
G01N 21/00 (2006.01)
G01N 21/27 (2006.01)
G01N 21/39 (2006.01)
G01N 21/31 (2006.01)

(52) U.S. Cl.
CPC .......... *G01N 21/274* (2013.01); *G01N 21/3103* (2013.01); *G01N 21/39* (2013.01); *G01N 2201/02* (2013.01); *G01N 2201/0612* (2013.01)

(58) Field of Classification Search
CPC . G01N 21/59; G01N 21/3504; G01N 21/274; G01N 2021/6482; G02F 1/157; Y10S 248/913
USPC ........ 356/244, 246, 432–440; 422/83, 88, 89; 250/573, 574, 576
See application file for complete search history.

(56) References Cited

U.S. PATENT DOCUMENTS

| 5,797,389 | A | * | 8/1998 | Ryder | A61M 11/06 128/200.21 |
| 5,912,734 | A | * | 6/1999 | Beck | G01B 11/27 356/301 |
| 8,482,735 | B2 | | 7/2013 | Okada | |
| 8,500,442 | B2 | | 8/2013 | Knittel et al. | |
| 2006/0038989 | A1 | * | 2/2006 | Domack | G01N 15/06 356/244 |
| 2013/0215412 | A1 | * | 8/2013 | Wynn | G01N 21/05 356/51 |

FOREIGN PATENT DOCUMENTS

JP 5336394 B2 11/2013
JP 5440524 B2 3/2014

* cited by examiner

*Primary Examiner* — Hoa Pham
(74) *Attorney, Agent, or Firm* — Osha Liang LLP

(57) ABSTRACT

An alignment unit for a laser analyzer that performs measurements on a substance inside a chamber includes a first alignment flange that attaches to the chamber, a second alignment flange that attaches one of a launch unit or detect unit of the laser analyzer to the chamber, an alignment stud for adjusting horizontal and vertical alignment of the second alignment flange, an optical window that keeps the chamber closed when the one of the launch unit or detect unit is removed from the chamber, and a sealing member provided between the second alignment flange and the optical window.

19 Claims, 3 Drawing Sheets

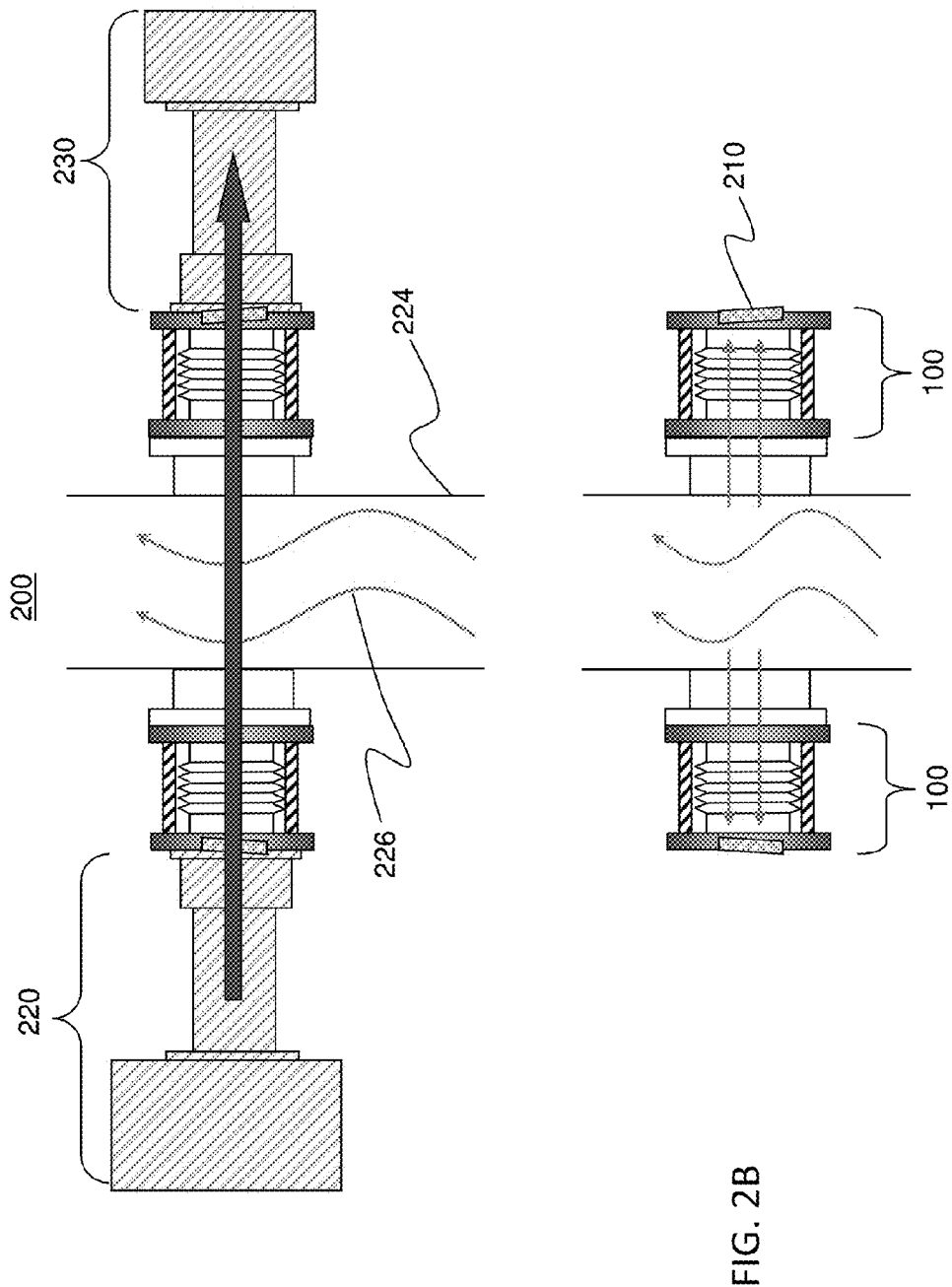

ALIGNMENT FLANGE MOUNTED OPTICAL WINDOW FOR A LASER GAS ANALYZER

FIELD OF DISCLOSURE

The present disclosure relates to a laser gas analyzer. In particular, embodiments of the invention relate to an alignment flange mounted optical window for a laser gas analyzer.

BACKGROUND

Laser analyzers are capable of determining the presence and/or concentration of components in a gas or liquid medium. Laser gas analyzers may use tunable diode laser absorption spectroscopy to measure the concentration of a high-temperature component, a component containing a corrosive gas, toxic gas, or the like. Such laser gas analyzers may operate by irradiating the component to be measured with light from a tunable diode laser with high component selectivity, in a non-contact manner, at high speed, and in real time without being subject to interference of other components.

Laser analyzers typically include a laser light source and a detector. The laser light source typically irradiates, for example, an atmosphere of a gas to be measured with measuring laser light. The detector detects the measuring laser light that has passed through the measuring space of the atmosphere of the gas to be measured. The laser gas analyzer measures an inherent light absorption spectrum of molecules, ranging from an infrared region to a near infrared region, by using a diode laser in which the emission wavelength spectral line width is extremely narrow. The molecule-inherent light absorption spectrum may correspond to molecule vibrations or rotation energy transitions. Inherent absorption spectra of many molecules including $O_2$, $NH_3$, $H_2O$, CO, and $CO_2$ are in the infrared to near infrared regions of the electromagnetic spectrum. The concentration of the target component may be calculated by determining the absorbed amount (absorbance) of light at a specific wavelength.

Laser gas analyzers may use a peak height method, 2f method, spectral area method or the like. For example, according to the peak height method, the concentration of a component to be measured is determined from the peak height of an absorption spectrum. In the 2f method, a wavelength signal for scanning is modulated to obtain a modulated waveform having a frequency twice the frequency of the wavelength signal. Then, the concentration of a component to be measured is determined based on a P-P (peak to peak) value of the modulated waveform. In the spectral area method, the absorption spectrum is measured while the emission wavelength of the laser is scanned to obtain the spectral area. The component concentrations may be calculated based on the spectral area. Unlike the other methods, the spectral area method may not be affected by variations of the pressure or coexisting gas components.

SUMMARY OF DISCLOSURE

In one aspect, according to one or more embodiments of the invention, a laser analyzer for performing measurements on a substance inside a chamber. The laser analyzer includes a launch unit with a diode laser that irradiates the substance with laser light, a detect unit with a light receiving element that detects the laser light having passed through the substance, and an alignment unit for removably connecting the launch unit or detect unit to the chamber. The alignment unit includes a first alignment flange that attaches to the chamber, a second alignment flange that attaches to the one of the launch unit or detect unit, and an alignment stud for adjusting horizontal and vertical alignment of the second alignment flange. The alignment unit also includes an optical window that keeps the chamber closed when the one of the launch unit or detect unit is removed from the chamber and a sealing member provided between the second alignment flange and the optical window.

Other aspects of the invention will be apparent from the following description and appended claims.

BRIEF DESCRIPTION OF DRAWINGS

FIG. 2A and FIG. 2B are schematics of an analyzer system in accordance with one or more embodiments of the invention. FIG. 2A is the analyzer system with the launch and detect units in accordance with one or more embodiments of the invention. FIG. 2B is the analyzer system without the launch and detect units in accordance with one or more embodiments of the invention.

DETAILED DESCRIPTION

Figure 1:
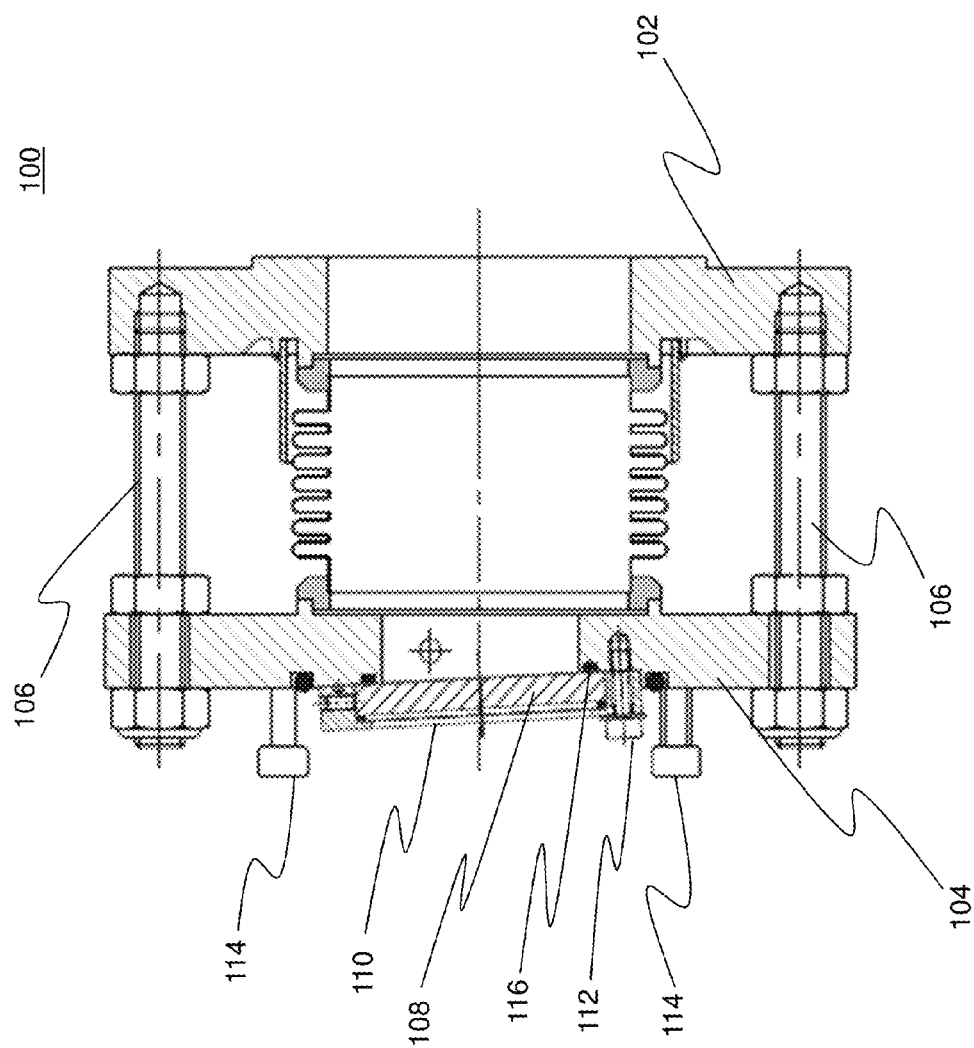
FIG. 1 is a schematic of an alignment unit in accordance with one or more embodiments of the invention.

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Embodiments of the invention relate to a laser analyzer, an alignment unit for a laser analyzer, and a laser analyzing system.

Generally, the principle of operation of a Tunable Diode Laser Spectroscopy Analyzer is based on absorption spectroscopy. Such analyzers may operate by measuring the amount of laser light that is absorbed as it travels through the substance being measured. The substance may include a gas or liquid.

One or more embodiments of the laser analyzer may include a launch unit that includes a laser system and a detect unit that includes a light receiving element, such as an optical detector. For example, the launch unit may include a tunable diode laser where the wavelength emission may be controlled based on the applied voltage and/or temperature of the diode, as known in the art. The detect unit may include a photodetector capable of detecting the light in the wavelength region emitted by the launch unit. For example, for near-infrared and infrared regions of the spectrum, an InGaAs (indium gallium arsenide) based detector may be used.

The launch unit and detect unit are removably connectable to a chamber containing the substance to be analyzed by the laser analyzer. The chamber need not necessarily be a vacuum chamber and may be a process pipe or vessel as known in the art. Both the launch unit and detect unit may be connected or mounted separately in accordance with one more embodiments of the invention. One or more embodiments of the laser analyzer may include an alignment unit to connect the detect unit to the chamber. One or more embodiments of the laser analyzer may also include a second alignment unit to connect the launch unit to the chamber. These alignment units are designed to facilitate the alignment of the laser through the chamber to optimize the signal in the detect unit in accordance with one or more embodiments of the invention.

In previous models of laser gas analyzers, an optical window may be included on the launch unit and detect unit to protect the laser or detector, particularly with regard to the detector, from exposure to the substance in the chamber, which may include a corrosive or dirty process gas. Furthermore, in previous models of laser gas analyzers, a valve was used on the alignment flange to prevent leakage of the process gas by closing the valve prior to calibration. However, in such systems, the substance in the chamber may still be released or leaked during offline calibration, maintenance, replacement or changing of the laser and detector, and the like. Such systems typically include additional parts, such as an inspection port, to attach to an alignment flange in place of the laser system or detector. Other systems may include an additional flange between the detector and the chamber that allows the chamber to be closed off prior to removal of the unit.

One or more embodiments of the laser analyzer include an alignment unit that includes an optical window. In one or more embodiments, the optical window allows for inspection inside the chamber, while preventing the substance from leaking out of the chamber. The alignment unit may facilitate the removal, inspection, and/or replacement of the launch and/or detect unit. In one or more embodiments, the optical window may be mounted at an angle to avoid direct reflection of the laser. For example, the optical window may be mounted at approximately 3 degrees relative to the laser beam. In one or more embodiments, the optical window may be used to inspect the inside of the chamber containing the substance to be interrogated.

In one or more embodiments of the invention, the alignment unit may be mounted in place around the chamber such that the launch and detect units are easily removable. Inspection through the optical window may provide information such as measurement gas condition, dust condition, and laser light characteristics emitted from launch side. Such improvements allow the substance inside the chamber to remain sealed, even if the detect unit and/or launch unit are removed.

FIG. 1 is a schematic of an alignment unit (100) in accordance with one or more embodiments of the invention. The alignment unit (100) includes a first alignment flange (102) that attaches to a chamber containing the substance to be interrogated by the analyzer. The alignment unit (100) may also include a second alignment flange (104) that attaches to the detect unit and/or launch unit. The relative position of the second alignment flange (104) may be adjusted using one or more alignment studs (106). As shown in FIG. 1, four alignment studs (106) may be used to adjust the relative positions of the first (102) and second (104) alignment flanges.

The second alignment flange (104) includes a window holder (108) that houses an optical window (110). The window holder (108) may be attached to the second alignment flange (104) by at least one screw (112). In the example shown in FIG. 1, the window holder (108) is attached to the second alignment flange (104) by at least three screws (112) in accordance with one or more embodiments of the invention. The screw (112) (or multiple screws) may be used to mount the optical window to the second alignment flange (104) in accordance with one or more embodiments of the invention.

One of ordinary skill in the art will appreciate that the window holder may be optional, as the optical window (110) may be directly incorporated into the second alignment flange (104).

The second alignment flange (104) of the alignment unit (100) may also include one or more quick connect screws (114) for connecting the alignment unit (100) to a quick connect plate of the detect unit or launch unit. The quick connect screws will be explained in more detail with respect to FIG. 3.

The second alignment flange (104) may also include a sealing member (116) provided between the second alignment flange (104) and the optical window (110), e.g., to secure a seal and prevent the substance from leaking on the launch unit or detect unit. In the example of FIG. 1, the sealing member (116) may include an O-ring or the like to facilitate the seal between the second alignment flange (104) and the optical window (110).

FIG. 2A and FIG. 2B are schematics of an analyzer system (200) in accordance with one or more embodiments of the invention. FIG. 2A demonstrates an analyzer system (200) that includes a launch unit (220) and a detect unit (230) in accordance with one or more embodiments of the invention. In the analyzer system (200), laser light that is generated in the launch unit (220) passes through an alignment unit (100) into a chamber (224) that contains the substance (226) to be analyzed. The laser light continues through the chamber (224) through the alignment unit (100) into the detect unit (230) where it is evaluated. The detect unit (230) may be connected to a computer system or processor (not shown) for the evaluation.

FIG. 2B is the analyzer system (200) shown with the launch unit (220) and the detect unit (230) removed from the system in accordance with one or more embodiments of the invention. As demonstrated in FIG. 2B, the launch unit (220) and/or the detect unit (230) may be removed, for example, to use the optical window (210) to inspect the inside of the chamber (224) or help troubleshoot absorption measurements. Also, as demonstrated in the example of FIG. 2B, the optical window (210) in the alignment unit (100) keeps the chamber (224) closed, meaning the chamber is sealed so that the substance (226) remains in the chamber (224).

The modular nature of the launch unit (220) and the detect unit (230) may facilitate the use of different laser emitters and detectors in the system in accordance with one or more embodiments of the invention. For example, a launch unit (230) may be characterized by the emission wavelength range emitted or the specific laser diode used, and the modular nature of launch unit may facilitate the changing of the wavelength range used to interrogate the substance (226).

Such considerations are also true for the detect unit (230) in accordance with one or more embodiments of the invention. For example, different optical detectors have different regions of sensitivity; therefore, the modular nature of the detect unit (230) may allow for quickly and easily changing the detector unit (230) in the system (200).

Figure 3B:
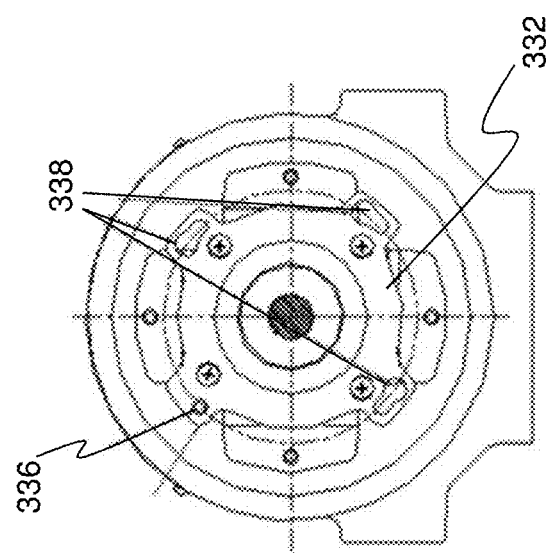
FIG. 3B is a schematic of a quick connect plate in accordance with one or more embodiments of the invention.
Figure 3A:
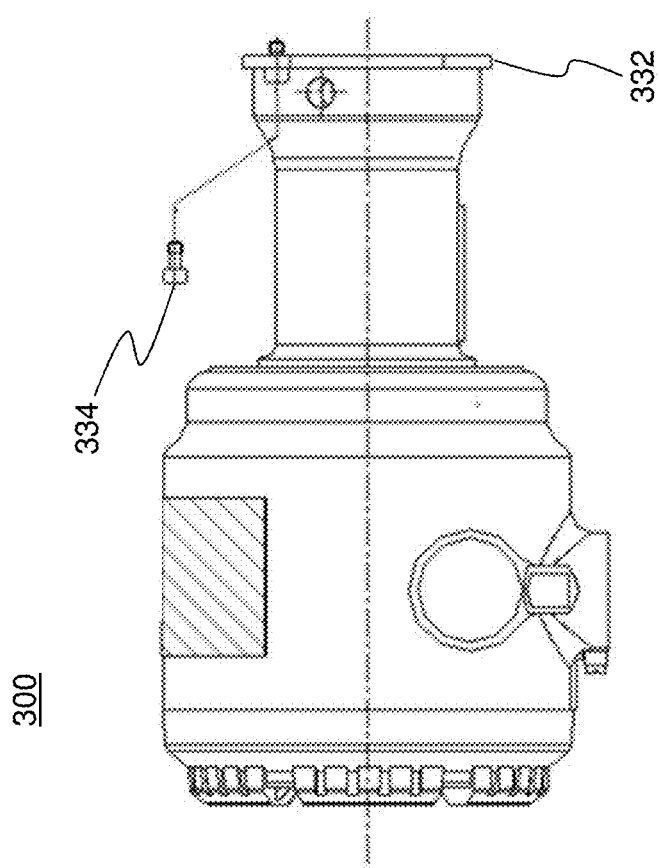
FIG. 3A is a schematic of a detect unit in accordance with one or more embodiments of the invention.

FIG. 3A is a schematic of a detect unit (330) in accordance with one or more embodiments of the invention. The detect unit (330) includes a quick connect plate (332) that connects the detect unit (330) to the alignment unit (not shown in FIG. 3). The detect unit (330) may also include one or more captive screws (334). For example, as demonstrated in FIG. 3A, the captive screw (334) may be permanently connected to the detect unit (330) to facilitate locking down the connection of the detect unit (330) to the alignment unit.

FIG. 3B is a schematic of the quick connect plate (332) in accordance with one or more embodiments of the invention.

As demonstrated in the example of FIG. 3B, the quick connect plate (332) includes a captive screw hole (336) to accommodate the captive screw (334) in accordance with one or more embodiments of the invention. The quick connect plate (332) may also include one or more hook slots (338). The hook slots (338) are designed to hook on to the one or more quick connect screws (114) shown in FIG. 1. For example, the detect unit (330) is connected to the alignment unit (100) by aligning the one or more quick connect screws (114) shown in FIG. 1 to the one or more hook slots (338) shown in FIG. 3B, and rotating the detect unit (330) to lock the one or more quick connect screws (114) into the hook locks (338). The detect unit (330) may then be locked in place by tightening the captive screw (334).

FIG. 3B shows three quick connect screws (114) and three hook slots (338), forming a square shape that includes the captive screw hole (336); however, embodiments of the invention are not limited to such. For example, the pattern of the one or more quick connect screws (114) and the quick one or more hook slots (338) may be specifically selected to allow the connection of certain different detect and/or launch units. In some embodiments, the aforementioned pattern may be different for a connection between a detect unit and an alignment unit as compared to a connection between a launch unit and an alignment unit. In other embodiments, the pattern may be the same for both connections.

One of ordinary skill in the art will appreciate that the connection mechanism of the detect unit (330) described above with respect to FIG. 3A and FIG. 3B may also be applied to the launch unit in accordance with one or more embodiments.

One or more embodiments of the invention advantageously provide an alignment unit that facilitates the removal/replacement of a detect unit without the exposure of the substance to be measured. One or more embodiments of the claimed invention advantageously provide an optical window in an alignment unit for observation into the system for various reasons, such as maintenance or alignment. With regard to maintenance, the optical window may allow a user to determine if any maintenance is required, such as cleaning the optical windows or the inside of the chamber containing a substance. One or more embodiments of the invention may also provide a modular system that may be used in a variety of applications. For example, different launch units may be correlated to different detect units, and such units may be interchangeable to obtain more absorption information quickly and efficiently.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A laser analyzer for performing measurements on a substance inside a chamber, comprising:
a launch unit comprising a diode laser that irradiates the substance with laser light;
a detect unit comprising a light receiving element that detects the laser light having passed through the substance; and
an alignment unit for removably connecting one of the launch unit or detect unit to the chamber, wherein the alignment unit comprises:
a first alignment flange that attaches to the chamber;
a second alignment flange that attaches to the one of the launch unit or detect unit;
an alignment stud for adjusting horizontal and vertical alignment of the second alignment flange;
an optical window that keeps the chamber closed when the one of the launch unit or detect unit is removed from the chamber; and
a sealing member provided between the second alignment flange and the optical window.

2. The laser analyzer of claim 1, wherein the optical window is angled relative to laser emission from the launch unit.

3. The laser analyzer of claim 1, wherein the one of the launch unit or detect unit further comprises a quick connect plate, and the alignment unit further comprises a quick connect screw that hooks into the quick connect plate.

4. The laser analyzer of claim 3, wherein the quick connect plate comprises:
a hook slot,
wherein the quick connect screw of the alignment unit hooks into the hook slot when the one of the launch unit or detect unit is connected to the alignment unit.

5. The laser analyzer of claim 1, further comprising:
a second alignment unit comprising:
a first alignment flange that attaches to the chamber;
a second alignment flange that attaches to the other of the launch unit or detect unit;
an alignment stud for adjusting horizontal and vertical alignment of the second alignment flange;
an optical window that keeps the chamber closed when the other of the launch unit or detect unit is removed from the chamber; and
a sealing member provided between the second alignment flange and the optical window.

6. The laser analyzer of claim 5, wherein the other of the launch unit or detect unit comprises a quick connect plate, and the second alignment unit further comprises a quick connect screw that hooks onto the quick connect plate.

7. The laser analyzer of claim 6, wherein the second quick connect plate is different from the quick connect plate.

8. The laser analyzer of claim 6, wherein the second quick connect plate comprises:
a hook slot,
wherein the quick connect screw of the second alignment unit hooks into the hook slot of the second quick connect plate when the other of the launch unit or detect unit is connected to the second alignment unit.

9. An alignment unit for a laser analyzer that performs measurements on a substance inside a chamber and that comprises a launch unit and a detect unit, the alignment unit comprising:
a first alignment flange that attaches to the chamber;
a second alignment flange that attaches one of the launch unit or detect unit to the chamber;
an alignment stud for adjusting horizontal and vertical alignment of the second alignment flange;
an optical window that keeps the chamber closed when the one of the launch unit or detect unit is removed from the chamber; and
a sealing member provided between the second alignment flange and the optical window.

10. The alignment unit of claim 9, wherein the optical window is angled relative to laser emission from the launch unit.

11. The alignment unit of claim 9, further comprising a quick connect screw that hooks into a hook slot on a quick connect plate on the one of the launch unit or detect unit when the one of the launch unit or detect unit is connected to the alignment unit.

12. A laser analyzer system for performing measurements on a substance inside a chamber, comprising:
- a modular launch unit comprising a diode laser that irradiates the substance with laser light;
- a modular detect unit comprising a light receiving element that detects the laser light having passed through the substance;
- an alignment unit for removably connecting one of the launch unit or detect unit to the chamber, wherein the alignment unit comprises:
  - a first alignment flange that attaches to the chamber;
  - a second alignment flange that attaches to the one of the launch unit or detect unit;
  - an alignment stud for adjusting horizontal and vertical alignment of the second alignment flange;
  - an optical window that keeps the chamber closed when the one of the launch unit or detect unit is removed from the chamber; and
  - a sealing member provided between the second alignment flange and the optical window.

13. The laser analyzer system of claim 12, wherein the optical window is angled relative to laser emission from the launch unit.

14. The laser analyzer system of claim 12, where the one of the launch unit or detect unit further comprises a quick connect plate, and the alignment unit further comprises a quick connect screw that hooks into the quick connect plate.

15. The laser analyzer system of claim 14, wherein the quick connect plate comprises:
- a hook slot,
- wherein the quick connect screw of the alignment unit hooks into the hook slot when the one of the launch unit or detect unit is connected to the alignment unit.

16. The laser analyzer system of claim 12, further comprising:
- a second alignment unit comprising:
  - a first alignment flange that attaches to the chamber;
  - a second alignment flange that attaches to the other of the launch unit or detect unit;
  - an alignment stud for adjusting horizontal and vertical alignment of the second alignment flange;
  - an optical window that keeps the chamber closed when the other of the launch unit or detect unit is removed from the chamber; and
  - a sealing member provided between the second alignment flange and the optical window.

17. The laser analyzer system of claim 16, wherein the other of the launch unit or detect unit comprises a second quick connect plate, and the second alignment unit further comprises a quick connect screw that hooks onto the quick connect plate.

18. The laser analyzer system of claim 17, wherein the second quick connect plate is different from the quick connect plate.

19. The laser analyzer system of claim 17, wherein the second quick connect plate comprises:
- a hook slot,
- wherein the quick connect screw of the second alignment unit hooks into the hook slot of the second quick connect plate when the other of the launch unit or detect unit is connected to the second alignment unit.

* * * * *